(12) United States Patent
Sang et al.

(10) Patent No.: US 12,160,682 B2
(45) Date of Patent: Dec. 3, 2024

(54) PLAYBACK METHODS FOR CONTRAST-ENHANCED ULTRASOUND MOVIE FILE AND ULTRASOUND MOVIE FILE AND ULTRASOUND APPARATUS

(71) Applicant: SHENZHEN MINDRAY BIO-MEDICAL ELECTRONICS CO., LTD., Guangdong (CN)

(72) Inventors: Maodong Sang, Shenzhen (CN); Jiexian Hou, Shenzhen (CN); Yunxia Huang, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 0 days.

(21) Appl. No.: 17/971,487

(22) Filed: Oct. 21, 2022

(65) Prior Publication Data
US 2023/0127820 A1    Apr. 27, 2023

(30) Foreign Application Priority Data
Oct. 26, 2021    (CN) .......................... 202111250203.2

(51) Int. Cl.
*H04N 5/92* (2006.01)
*A61B 8/00* (2006.01)
(Continued)

(52) U.S. Cl.
CPC ............... *H04N 5/92* (2013.01); *A61B 8/461* (2013.01); *A61B 8/481* (2013.01); *G11B 27/005* (2013.01)

(58) Field of Classification Search
CPC .......... H04N 5/92; H04N 5/783; A61B 8/461; A61B 8/481; A61B 8/465; A61B 8/463;
(Continued)

(56) References Cited

U.S. PATENT DOCUMENTS 11,672,512 B2 *  6/2023  Luo ........................ A61B 8/461
                                              600/458
2020/0155121 A1 *  5/2020  Kwon .................... A61B 8/467
(Continued)

FOREIGN PATENT DOCUMENTS

| CN | 101732072 A | 6/2010 |
|---|---|---|
| CN | 102641134 A | 8/2012 |
| CN | 111417347 A | 7/2020 |

*Primary Examiner* — Helen Shibru
(74) *Attorney, Agent, or Firm* — Sheppard Mullin Richter & Hampton LLP

(57) ABSTRACT

Disclosed are a method for playing a CEUS movie file, an ultrasound movie file, and ultrasound apparatus. The method comprises: receiving a playing instruction for the movie file which is a dynamic data of generated by ultrasound echoes returned from a target tissue to which ultrasound waves are transmitted by a probe of an ultrasound apparatus; determining an imaging frame rate of the ultrasound images; determining a playback frame rate of the movie file according to the imaging frame rate negatively correlated with the playback frame rate; and playing the movie file with the playback frame rate. By using the playback frame rate which is negatively correlated with the imaging frame rate to play movie files, the movie files with low frame rate can be played more smoothly and the movie files with high frame rate can be played in line with the look and feel of the human eye.

14 Claims, 4 Drawing Sheets

(51) Int. Cl.
*A61B 8/08* (2006.01)
*G11B 27/00* (2006.01)

(58) Field of Classification Search
CPC .. A61B 8/54; A61B 8/44; A61B 8/483; A61B 8/5215; G11B 27/005
USPC .......................................................... 386/353
See application file for complete search history.

(56) References Cited

U.S. PATENT DOCUMENTS

| | | |
|---|---|---|
| 2020/0281571 A1 | 9/2020 | Luo et al. |
| 2023/0240660 A1* | 8/2023 | Luo ...................... A61B 8/5207 600/458 |

* cited by examiner

PLAYBACK METHODS FOR CONTRAST-ENHANCED ULTRASOUND MOVIE FILE AND ULTRASOUND MOVIE FILE AND ULTRASOUND APPARATUS

CROSS REFERENCE TO RELATED APPLICATIONS

This application is based on and claims priority to and benefits of Chinese Patent Application No. 202111250203.2, filed on Oct. 26, 2021. The entire content of the above-identified application is incorporated herein by reference.

TECHNICAL FIELD

The present disclosure relates to contrast enhanced ultrasound (CEUS) imaging, and more particularly, to methods for playing a CEUS movie file, methods for playing an ultrasound movie file, and ultrasound apparatus.

BACKGROUND OF THE INVENTION

Ultrasound can penetrate deep into tissues without causing tissue damage, making it ideal for non-invasive biomedical imaging. When encountering a scatterer, ultrasound may be scattered, and the scattering intensity thereof is related to the size and shape of the scatterer, as well as the difference of acoustic impedance between the scatterer and the surrounding tissue. Taking blood as an example, the scattering of blood to ultrasound is very weak, so an "anechoic" symbol may be appeared on ordinary ultrasonic instruments in case of blood scattering ultrasound. In order to enhance the scattering of ultrasound by blood, a medium (microbubbles) with different acoustic impedance from blood is added to the blood, and the scattering in the blood will be enhanced. CEUS imaging for tissue is to inject an ultrasound contrast agent, that is, a solution containing microbubbles, into the body, and the contrast agent enters organs and tissues to develop or enhance the imaging of the organs and tissues, thereby providing an important basis for clinical diagnosis.

In recent years, CEUS imaging has played an increasingly important role in the differential diagnosis and ablation assessment of cardiovascular, liver, thyroid, and breast diseases. Taking liver tumors as an example, compared with normal tissues, the micro-blood flow in malignant tumors is often more abundant, and the typical manifestation of its CEUS images is that the microbubbles in the focus region enter and subside faster than those in normal tissues. Generally speaking, in order to distinguish this hemodynamic difference between normal tissues and malignant tissues, CEUS is required to have a certain imaging frame rate.

For different tissues and different diseases, the imaging modes adopted in ultrasound imaging may be various, as well as their corresponding imaging frame rate. The existing dynamic data playback methods of ultrasound images usually directly play with the imaging frame rates corresponding to the imaging modes; however, the playback effect thereof may be subjected to too high or too low imaging frame rates, thereby affecting user experience.

SUMMARY OF THE INVENTION

A purpose of the present application is to overcome at least one problem in the prior art and provide methods for playing a CEUS movie file, methods for playing an ultrasound movie file, and ultrasound apparatus.

In one of the embodiments, a method for playing an ultrasound movie file is provided, comprising:
receiving a playing instruction for the movie file;
the movie file being the dynamic data of contrast-enhanced images, the contrast-enhanced images being generated by ultrasound echoes which are acoustic signals returned from a target tissue to which ultrasound waves are transmitted by a probe of a contrast-enhanced ultrasound apparatus according to an imaging mode, the imaging mode including a first imaging mode and a second imaging mode, and an imaging frame rate corresponding to the first imaging mode being greater than an imaging frame rate corresponding to the second imaging mode;
determining an imaging mode of the movie file;
determining a playback frame rate of the movie file according to the imaging mode of the movie file; and
playing the movie file with the playback frame rate;
when the imaging mode of the movie file is the first imaging mode, determining the playback frame rate of the movie file as a first playback frame rate according to the first imaging mode, and the first playback frame rate being than the imaging frame rate corresponding to the first imaging mode.

When playing a movie file consisting of contrast enhanced images of high frame rate that are generated based on a high frame rate contrast enhanced imaging mode (the first imaging mode), the movie file is played at a frame rate lower than the imaging frame rate, avoiding the situations of affecting a user's viewing experience where the playback frame rate is too high, the dwell time on each frame of contrast enhanced image is short, and detailed information in each image cannot be effectively displayed to the user.

In one of the embodiments, a method for playing an ultrasound movie file is provided, comprising:
receiving a playing instruction for the movie file, the movie file being a dynamic data of ultrasound images, the ultrasound images being generated by ultrasound echoes which are acoustic signals returned from a target tissue to which ultrasound waves are transmitted by a probe of an ultrasound apparatus;
determining an imaging frame rate of the ultrasound images;
determining a playback frame rate of the movie file according to the imaging frame rate of the ultrasound images, the imaging frame rate of the ultrasound images being negatively correlated with the playback frame rate of the movie file; and
playing the movie file with the playback frame rate.

By adjusting the playback frame rate with the imaging frame rate corresponding to the imaging mode of the movie file, the imaging frame rate is negatively correlated with the playback frame rate, avoiding being unable to present effectively detailed information in each image to the user due to short dwell time on each frame of contrast enhanced image; and on the contrary, the dwell time on each frame of contrast enhanced image is too long due to too low imaging frame rate, which leads to slow playback speed and improves the user's viewing experience.

In one of the embodiments, an ultrasound apparatus is provided, comprising: a probe, a transmitting circuit, a receiving circuit, a beam synthesis circuit, a memory, and a processor configured to execute the steps of the method for playing a contrast enhanced ultrasound movie file /an ultrasound movie file according to any one of the aforesaid embodiments.

BRIEF DESCRIPTION OF THE DRAWINGS

In order to illustrate the technical solutions in the embodiments of the present invention more clearly, the following briefly introduces the accompanying drawings used in the description of the embodiments. Obviously, the accompanying drawings in the following description are only some embodiments of the present invention. For those of ordinary skill in the art, other drawings can also be obtained from these drawings without creative labor.

DETAILED DESCRIPTION

In order to make the objectives, technical solutions, and advantages of the present application more clear, example embodiments according to the present application will be described in detail below with reference to the accompanying drawings. Apparently, the described embodiments are merely some rather than all of the embodiments of the present application. It should be understood that the example embodiments described herein do not constitute any limitation to the present application. All other embodiments derived by those skilled in the art without creative efforts on the basis of the embodiments of the present application described in the present application shall fall within the scope of protection of the present application.

In the following description, a large number of specific details are given to provide a more thorough understanding of the present application. However, it would be understood by those skilled in the art that the present application can be implemented without one or more of these details. In other examples, to avoid confusion with the present application, some technical features known in the art are not described.

It should be understood that the present application can be implemented in different forms and should not be construed as being limited to the embodiments presented herein. On the contrary, these embodiments are provided to make the disclosure thorough and complete, and to fully convey the scope of the present application to those skilled in the art.

The terms used herein are intended only to describe specific embodiments and do not constitute a limitation to the present application. When used herein, the singular forms of "a", "an", and "said/the" are also intended to include plural forms, unless the context clearly indicates otherwise. It should also be appreciated that the terms "comprise" and/or "include", when used in the specification, determine the existence of described features, integers, steps, operations, elements, and/or units, but do not exclude the existence or addition of one or more other features, integers, steps, operations, elements, units, and/or groups thereof. As used herein, the term "and/or" includes any and all combinations of relevant listed items.

For a thorough understanding of the present application, detailed steps and detailed structures will be provided in the following description to explain the technical solutions proposed by the present application. The preferred embodiments of the present application are described in detail as follows. However, in addition to these detailed descriptions, the present application may further have other implementations.

Figure 1:
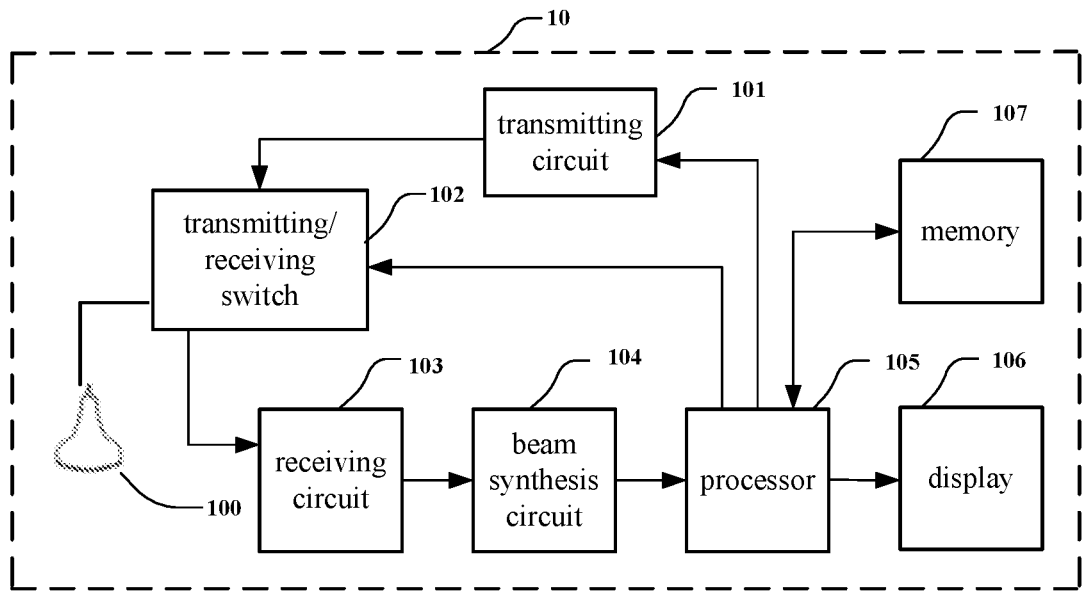
FIG. 1 is a schematically structural diagram of an ultrasound apparatus in an embodiment.

Please refer to FIG. 1, a schematic block diagram of an ultrasound apparatus in an embodiment of the present application. The ultrasound apparatus 10 may include a probe 100, a transmitting circuit 101, a transmitting/receiving switch 102, a receiving circuit 102, a beam synthesis circuit 104, a processor 105 and a display 106. The transmitting circuit 101 may excite the probe 100 to transmit ultrasound waves to a target tissue containing a contrast agent; and the receiving circuit 103 may receive ultrasound echoes returned from the target tissue through the probe 100 to obtain ultrasound echo signals which are processed by the beam synthesis circuit 104 and then sent to the processor 105. The processor 105 may the data obtained after process the process of beam synthesis to obtain an ultrasound image of the target tissue. The ultrasound image obtained by the processor 105 may be stored in the memory 107, and may be shown on the display 106.

In one embodiment of the present application, the display 106 of the aforementioned ultrasound apparatus 10 may be a touch display screen, a liquid crystal display screen and the like, or may be an independent display device (such as a liquid crystal display, a television, etc.) independent of the ultrasound apparatus 10, or displays on electronic devices such as mobile phones, tablets, etc.

In practical applications, the processor 105 may be at least one of an application specific integrated circuit (ASIC), a digital signal processor (DSP), a digital signal processing device (DSPD), a programmable logic device (PLD), a field programmable gate array (FPGA), a central processing unit (CPU), a controller, a microcontroller, and a microprocessor, so that the processor 105 can execute corresponding steps of the ultrasound imaging method in the various embodiments of the present application. The memory 107 may be a volatile memory (volatile memory), such as a random access memory (RAM), or a non-volatile memory, such as a read only memory (ROM), flash memory, hard disk drive (HDD) or solid-state drive (SSD), or a combination of the above types of memory, and may provide instructions and data to the processor.

Figure 2:
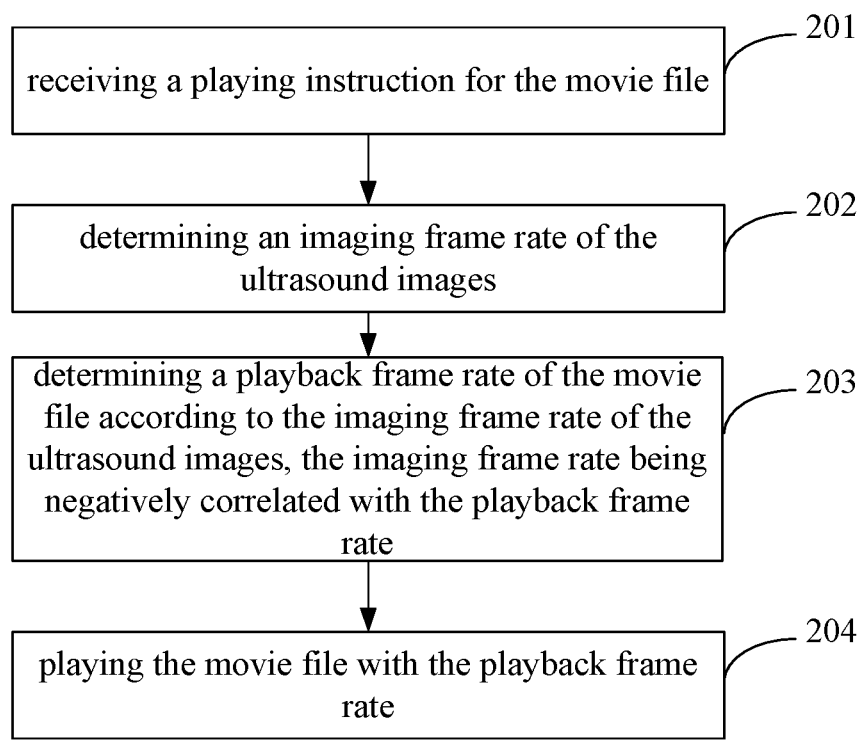
FIG. 2 is a schematic flowchart of a method of playing an ultrasound movie file in an embodiment.

Referring to FIG. 2, a method for playing an ultrasound movie file provided in one embodiment may include specific steps as follows:

Step 201: receiving a playing instruction for the movie file.

In the specific embodiment, the movie file may be the dynamic data of the ultrasound image. The ultrasound image is generated according to ultrasound echoes which are sound wave signals returned from the target tissue to which ultrasound waves are transmitted by the probe of the ultrasound apparatus. The ultrasound images include, but are not limited to, B-mode images, contrast-enhanced images, and images acquired by elasticity imaging.

The movie file may be played on the ultrasound apparatus or on other equipment that may play CEUS data. For the convenience of explanation, it is taken as an example that a movie file is played on the ultrasound apparatus. The playing instruction is a computer instruction for instructing to play a movie file. The computer instruction may be an instruction automatically generated by the ultrasound apparatus according to user input, or may be an instruction sent by other terminal devices to the ultrasound apparatus. The user input may include, but is not limited to, voice input, a click operation on a movie file, and the like. The ultrasound apparatus 10 may receive the playing instruction generated according to the user input, or receive playing instructions sent from other terminal devices to the ultrasound apparatus 10.

Step 202: determining an imaging frame rate of the ultrasound images.

The imaging frame rate of the ultrasound images may be related to parameters including imaging depth, the number of transmissions per frame, and sound speed, and may be adjusted by adjusting the parameters. That is, when the parameters are fixed, the imaging frame rate of the ultrasound images is fixed. Different tissues and organs have different requirements on the imaging frame rates of ultrasound images, and the imaging frame rates of different dimensions are also different. The imaging frame rates at present may be mainly divided into three categories: conventional 2D imaging frame rate, 2D high frame rate, and 3D/4D volume rate. The conventional 2D imaging frame rate which may be 10-15 frames per second is usually lower than the 2D high frame rate which may be tens to hundreds of frames per second, and the 3D/4D volume rate which may generally be 1-5 volumes per second is usually smaller than the 2D imaging frame rate.

Step 203: determining a playback frame rate of the movie file according to the imaging frame rate of the ultrasound images, the imaging frame rate of the ultrasound images being negatively correlated with the playback frame rate of the movie file.

Step 204: playing the movie file with the playback frame rate.

The playback frame rate may refer to the frame rate of playing the movie file, such as playing 10, 30 or 35 frames per second, etc. In this embodiment, different imaging frame rates correspond to different playback frame rates, and the playback frame rate is negatively correlated with the imaging frame rate of the ultrasound images, that is, the larger the imaging frame rate is, the smaller the playback frame rate is, and the smaller the imaging frame rate is, the larger the playback frame rate is Similar to playing a movie file generated by fast-speed imaging in a "slow down" mode, a movie file generated by slow-speed imaging is played in a "speed up" mode. When a movie file generated by fast-speed imaging is played at the same playback frame rate as the imaging frame rate, it cannot provide the human eye with a feeling that the frame rate is increased several times. For a movie file generated by slow-speed imaging, human may perceive sluggish playback including "frame skipping" and "not smooth" caused by the low frame rate, resulting in a poor look and feel. Playing the movie file generated by fast-speed in a "slow down" mode and playing the movie file generated by slow-speed in a "speed up" mode can improve the look and feel of the movie files.

In one embodiment, when the playback frame rate of the movie file is determined according to the imaging frame rate of the ultrasound images, the playback frame rate may be directly or indirectly determined according to the imaging frame rate. Determining the playback frame rate directly means that the imaging frame rate is directly related to the playback frame rate, and determining indirectly means that the imaging frame rate and the playback frame rate are related by other parameters.

In one embodiment, when the playback frame rate of the movie file is determined according to the imaging frame rate of the ultrasound images, the imaging frame rate may be divided into intervals, and imaging frame rates in different intervals correspond to different playback frame rates. The imaging frame rate in one interval corresponds to one playback frame rate, multiple playback frame rates or playback frame rate intervals. When it corresponds to multiple playback frame rates or playback frame rate intervals, the user can also choose independently or customize playback frame rate within the interval. In this way, user interaction can be increased and product experience can be improved.

In one embodiment, when the playback frame rate of the movie file is determined according to the imaging frame rate of the ultrasound images, it may also be automatically calculated according to a calculation method of the imaging frame rate corresponding to the imaging mode of each movie file and a customized playback frame rate. The input of this calculation method is the imaging frame rate, and the output thereof is the playback frame rate. The playback frame rate may be obtained by, for example, adding a fixed value to the imaging frame rate or subtracting a fixed value from the imaging frame rate, or by multiplying the imaging frame rate with a coefficient. By using a set calculation method to adaptively adjust the playback frame rate upon the imaging frame rate, the user experience can be improved without human intervention, making the operation more convenient.

In the aforesaid method for playing the ultrasound movie files, the playback frame rate may be adjusted according to the imaging frame rate corresponding to the imaging mode of the movie file; that is, the movie file with high imaging frame rate is played at a frame rate lower than the imaging frame rate, and the movie file with lower imaging frame rate is played at a frame rate higher than the imaging frame rate. In this respect, problems in the existing playback, including the problem of poor look and feel (such as not smooth, frame skipping, etc. that mentioned above) caused by using imaging frame rate directly as the playback frame rate to play the movie file of low frame rate, as well as the problem of poor look and feel caused by fast update of the content of the movie file when playing the movie file of high frame rate, can be solved.

In one embodiment, step 203 may include: calculating a difference between the imaging frame rate and a preset frame rate; when the difference is within a first threshold interval and the imaging frame rate is greater than the preset frame rate, determining that the playback frame rate is less than the imaging frame rate; and when the difference is within a second threshold interval and the imaging frame rate is less than the preset frame rate, determining that the playback frame rate is greater than the imaging frame rate.

The preset frame rate and threshold intervals may be user-defined or factory preset. The preset frame rate and threshold intervals customized by users can make corresponding set value more in line with users' habits. The lower limit of the first threshold interval may be greater than or equal to the upper limit of the second threshold interval. Whether the movie file is played slowly or fast is determined according to the threshold interval in which the difference is located. When the difference is within the first threshold interval, it means that the imaging frame rate corresponding to the imaging mode of the movie file is relatively large, so that the playback frame rate of the movie file is smaller than the imaging frame rate, achieving the effect of slow playback of the movie file. When the difference is within the second threshold interval, it means that the imaging frame rate corresponding to the imaging mode of the movie file is relatively small, so that the playback frame rate of the movie file is greater than the imaging frame rate, achieving the effect of fast playback of the movie file.

In one embodiment, step 203 may further include: when the difference is within a third threshold interval, determining that the playback frame rate is equal to the imaging frame rate of the ultrasound images or to the preset frame rate; wherein an upper limit of the third threshold interval is less than or equal to the lower limit of the first threshold interval, and a lower limit of the third threshold interval is greater than or equal to an upper limit of the first threshold interval.

The third threshold interval is an interval between the first threshold interval and the second threshold interval. This interval can be user-defined or factory set. When the imaging frame rate is within the third threshold interval, it means that the imaging frame rate in this interval can be directly used for playback, so the imaging frame rate in this interval can be directly used as the playback frame rate, or the preset frame rate can be used as the playback frame rate of the movie file whose imaging frame rate is within the third threshold interval. The imaging frame rate may be further divided, so that the movie file can be played more diversely, thereby improving the user experience.

In one embodiment, step 203 includes: determining a playback speed level according to the imaging frame rate of the ultrasound images, a playback speed corresponding to the playback speed level being negatively correlated with the imaging frame rate of the ultrasound images; and calculating the playback frame rate according to the playback speed level and the imaging frame rate of the ultrasound images.

The playback speed level may be used to adjust the playback levels of the movie file. By adjusting the speed level, the playback frame rate of the movie file can be adjusted to achieve fast playback or slow playback of the movie file. Different imaging frame rates correspond to different playback speed levels, wherein one imaging frame rate may correspond to one or more playback speed levels or playback speed level intervals. When it corresponds to only one level, the only one playback speed level corresponding to the imaging frame rate may be used as the speed level for playing the movie file; and when it corresponds to more levels, the user may choose or customize it. The playback speed corresponding to the playback speed level is negatively correlated with the imaging frame rate of the ultrasound images. That is, fast playback speed corresponds to small imaging frame rate, and slow playback speed corresponds to large imaging frame rate. In this way, a fast-motion effect can be achieved by using a faster playback speed to play a movie file with a small imaging frame rate, and a slow-motion effect can be achieved by using a slower playback speed to play a movie file with high imaging frame rate.

When calculating the imaging frame rate and the playback speed level, the specific calculation thereof may include, but not limit to, multiplying the imaging frame rate directly by the playback speed corresponding to the playback speed level, or performing other calculations after the multiplication (such as adding a fixed value to the product of the multiplication, or rounding the product, etc.), or processing the imaging frame rate and playback speed before multiplying.

In one embodiment, step 203 may include: determining a playback speed level according to the imaging frame rate of the ultrasound images, a playback speed corresponding to the playback speed level being negatively correlated with the imaging frame rate of the ultrasound images; and taking a preset playback frame rate corresponding to the playback speed level as the playback frame rate.

The playback speed level and the playback speed corresponding to the playback speed level are negatively correlated with the imaging frame rate of the ultrasound images, which is the same as those described above, and will not be repeated here. The playback speed level may directly correspond to the playback frame rate. That is, one playback speed level may correspond to one playback frame rate, multiple playback frame rates, or playback frame rate intervals. When corresponding to one playback frame rate, the playback frame rate may be directly used as the frame rate for playing the movie file; and when corresponding to multiple, the user may select or customize the playback frame rate corresponding to the playback speed level.

In one embodiment, determining the playback speed level according to the imaging frame rate of the ultrasound images may include: determining the playback speed level from a plurality of preset playback speed levels according to the imaging frame rate of the ultrasound images.

The preset playback speed levels may be pre-stored on the ultrasound apparatus 10 which may also store the correlation between the imaging frame rates and the preset playback speed levels. After the imaging frame rate is determined, a playback speed level corresponding to the determined imaging frame rate is directly searched from the preset playback speed levels according to the stored correlation. When there is a unique preset playback speed level corresponding to the imaging frame rate, the preset playback speed level may be directly served as the playback speed level of the movie file.; and when there are multiple preset playback speed levels corresponding to the imaging frame rate, the corresponding preset playback speed may be prompted in a specific way that is not limited herein, including directly illustrated on the display 106, or using voice, etc. The user may select a final playback speed level according to the prompt, or customize the playback speed level according to the prompt.

In one embodiment, determining the playback speed level from a plurality of preset playback speed levels according to the imaging frame rate of the ultrasound images may include: determining a candidate playback speed level from the plurality of preset playback speed levels according to the imaging frame rate of the ultrasound images; and determining the playback speed level from the candidate playback speed level according to input information of a user input interface.

The candidate playback speed level may be configured to provide preset playback speed levels for users to select, wherein when the imaging frame rate is large, the playback speed corresponding to the candidate playback speed level is slow, and when the imaging frame rate is small, the playback speed corresponding to the candidate playback speed level is fast. The user interface is for enabling interaction with the ultrasound apparatus 10. The user interface may be used to realize the operation of selecting the candidate playback speed level to determine the playback speed level according to the selecting operation. With the determination of the candidate playback speed level from the playback speed levels by the imaging frame rate, the range of selectable parameters can be reduced, facilitating user selection and saving interaction costs.

In one embodiment, all preset playback speed levels or only the candidate playback speed level are prompted in an unlimited manner. When prompting all preset speed playback speed levels, the prompts for the candidate playback speed level may be the same as or different from the prompts for other than the candidate playback speed level. By using different prompting manners, it can be easy for users to distinguish between selectable levels and unselectable levels, which is convenient for users to choose.

In one embodiment, the candidate playback speed level may be displayed. The candidate playback speed level may be shown on the display 106.

In another embodiment, the preset playback speed levels other than the candidate playback speed level may be displayed under a first display mode, and the candidate playback speed level may be displayed under a second display mode that is different from the first display mode.

All preset playback speed levels are displayed on the display 106. The first display mode is different from the second display mode; for example, the levels displayed under the first display mode that is only for displayed cannot be operated by users, while the levels displayed under the second display mode can be operated; or for another example, different color codes are used for display under the two display modes; or the two display modes can be distinguished by a combination of color and operation. By using different display modes, it can be easy for users to distinguish between selectable levels and unselectable levels, which is convenient for users to choose, saving interaction costs.

In one embodiment, step 204 may include: playing the movie file in a loop manner with the playback frame rate.

When the movie file is not paused or stopped after being started to play, it can be played repeatedly; that is, when the last image frame of the movie file is played, the next image frame to be played is the first image frame of the movie file. The number of times the movie file loops can be set by users according to their requirements. Alternatively, the movie file may be played in a loop manner with a default number of loops.

In one embodiment, during automatically playing the movie file, the playback of the movie file can be intervened by users at any time, such as pausing playback, stopping playback, switching playback mode, adjusting playback frame rate, and the like.

In one embodiment, during playing the movie file with the playback frame rate, the method may further comprise: switching a playback mode of the movie file from an automatic playing mode to a manual playing mode based on a first switching instruction; and playing image frames of the movie file under the manual playing mode.

During the automatic playback of the movie file, the playback mode can be switched at any time by users. The first switching instruction may be a computer instruction for switching the playback mode. When the instruction is received, the playback mode of the movie file is switched from the automatic playing mode to the manual playing mode. After switching the playback mode, the movie file is played based on manual operation by users.

In one embodiment, when it is detected that a certain image frame being played during automatic playback meets a preset condition, the playback mode of the movie file may be directly switched to the manual playing mode. The preset condition may be set in the factory, or be a condition determined by learning the users' usage habits or collected data, or be a condition set by the users independently. When a parameter of a certain tissue or organ is recognized as an abnormality in the image, the playback mode may be automatically switched.

In one embodiment, playing image frames of the movie file under the manual playing mode may comprise: when a preset operation for a control panel is detected, in response to the preset operation, playing the image frames of the movie file at a playback speed corresponding to the preset operation, wherein the playback speed is positively correlated with an operating speed of the preset operation.

The control panel may include knobs, trackballs, and touchscreens, among others. The control panel may be used to receive user operations. The preset operation may be a predefined operation, and different preset operations correspond to different operation instructions. When it is detected that the user's operation on the knob, trackball or touch screen is the preset operation, a corresponding instruction may be generated according to the preset operation, and the instruction is responded to. The presets may include, but be not limited to, a rotation operation on a knob, a rolling operation on a trackball, and a sliding operation on a touch screen. When detecting the preset operation, the operation duration and the operation displacement of the preset operation may be detected, and the operation speed may be determined according to the operation duration and the operation displacement. The playback speed is positively correlated with the operation speed of the preset operation, which means that the faster the user's operation speed is, the faster the playback speed is. For example, by quickly rotating the knob or rolling the trackball or sliding on the touch screen by the user, the fast-motion effect of the movie file can be achieved, and by slowly rotating the knob or rolling the trackball or sliding on the touch screen by the user, the slow-motion effect of the movie file can be achieved.

In one embodiment, the preset operation may further include an operation direction configured to determine whether the movie file is played forward or backward, and different operation directions correspond to different play directions. The corresponding relationship between the operation direction and the forward or backward playback of the movie can be customized by the user. For example, when the knob is rotated counterclockwise, it means playing backward, and when the knob is rotated clockwise, it means playing forward. For another example, sliding the touch screen up or right means playing forward, and sliding down or left means playing backward, etc.

In one embodiment, a playing speed corresponding to the manual playing mode is lower than a playing speed corresponding to the automatic playing mode. The playback speed corresponding to the manual playing mode is lower than that of the automatic playing mode, in order to facilitate the user to better watch the details of the movie file. That is, if users want to view the movie file carefully, the maximum playback speed of manual playback can be limited to be smaller than the speed of automatic playback. Taking the trackball as an example, when each image frame of the movie file is switched by rotating the trackball by users, the switching time of each image frame is greater than the preset time threshold regardless of the rotation speed. In this way, too short dwell time on each image frame of the movie file due to too fast rotation of the trackball can be avoided, improving users' viewing.

In one embodiment, the ultrasound image is based on transmitting an ultrasound echo to the target tissue according to an imaging mode of the ultrasound apparatus, the imaging mode include a first imaging mode and a second imaging mode, the imaging frame rates of the first imaging mode and the second imaging mode are different, the imaging frame rate corresponding to the first imaging mode is greater than the imaging frame rate corresponding to the second imaging mode, and the first imaging mode and the second imaging mode correspond to imaging in different time periods in same contrast-enhanced imaging performed on tissues.

In one embodiment, the ultrasound apparatus provided with a CEUS imaging function, and when performing CEUS imaging on human tissue or organs, there may include at least two imaging modes in the same contrast-enhanced imaging process, that is, at least a first imaging mode and a second imaging mode. The imaging speed of the first imaging mode is faster than that of the second imaging mode, and the imaging speed may be pre-configured or determined by the user by adjusting parameters or selecting the mode before starting performing contrast enhanced imaging.

In one embodiment, the first imaging mode is used in a wash-in stage of a contrast agent, and the second imaging mode is used in a stage other than the wash-in stage of the contrast agent. In order to observe the wash-in process of contrast microbubbles more carefully, it is necessary to use a higher imaging frame rate for imaging in the wash-in stage of contrast microbubbles, and the imaging mode corresponding to the imaging frame rate lower than that required in the wash-in stage can be chosen to use in other stages. By using high frame rate to acquire the contrast image data in wash-in stage and relatively low frame rate to acquire the contrast image data in other stages, a better balance between rich contrast-enhanced data and the amount of data processing can be achieved, and with preference to the capacity of equipment and data processing capability of conventional ultrasound apparatus, the contrast-enhanced imaging data can be processed at a faster speed without sacrificing data in important stages.

In one embodiment, the wash-in stage of the contrast agent comprises a stage corresponding to formation of contrast agent microbubbles. In the wash-in process of contrast agent, the process corresponding to formation of the contrast agent microbubbles is a relatively important process; therefore in the wash-in process of contrast agent, at least the imaging mode with high frame rate should be used to collect the process corresponding to formation of the contrast agent microbubbles, so as to enrich the data volume of the process and balance the processing speed of the apparatus.

Figure 3:
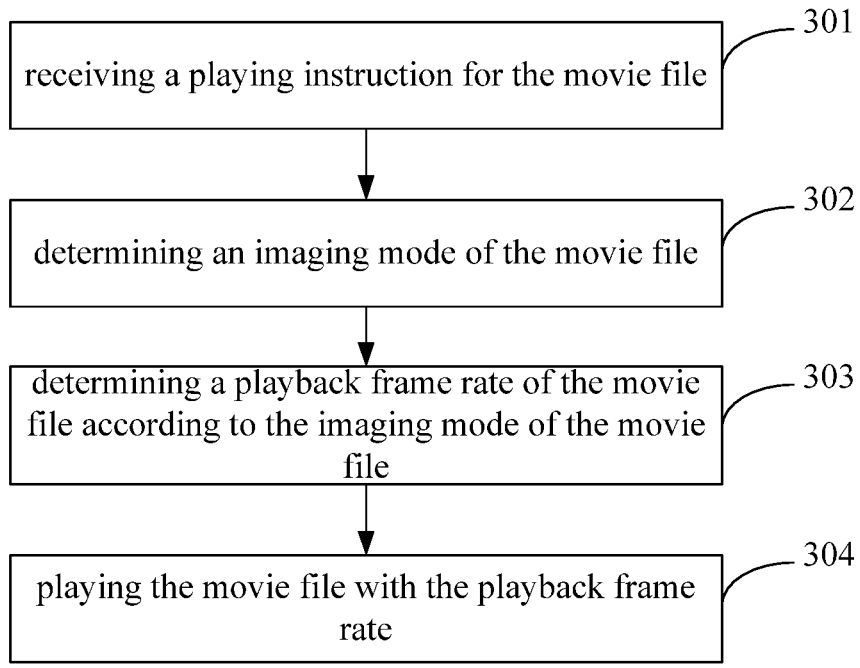
FIG. 3 is a schematic flowchart of a method of playing a CEUS movie file in an embodiment.

Referring to FIG. 3, a method for playing a CEUS movie file provided in one embodiment may include specific steps as follows:

step 301: receiving a playing instruction for the movie file;

In the specific embodiment, the movie file may be the dynamic data of contrast-enhanced images, the contrast-enhanced images may be generated by ultrasound echoes which are acoustic signals returned from a target tissue to which ultrasound waves are transmitted by a probe of a CEUS apparatus according to an imaging mode, the imaging mode may include a first imaging mode and a second imaging mode, and an imaging frame rate corresponding to the first imaging mode may be greater than an imaging frame rate corresponding to the second imaging mode.

Step 302: determining an imaging mode of the movie file.

Step 303: determining a playback frame rate of the movie file according to the imaging mode of the movie file.

Step 304: playing the movie file with the playback frame rate.

In the specific embodiment, when the imaging mode of the movie file is the first imaging mode, the playback frame rate of the movie file may be determined as a first playback frame rate according to the first imaging mode, and the first playback frame rate may be smaller than the imaging frame rate corresponding to the first imaging mode.

The words appearing in this embodiment have the same meanings as those in the above-mentioned embodiments, and will not be repeated here. The first imaging mode and the second imaging mode are two different contrast-enhanced imaging modes on the CEUS apparatus in this embodiment, and the imaging frame rate corresponding to the first imaging mode is higher than that of the second imaging mode.

In one embodiment, the imaging frame rate corresponding to the second imaging mode is a frame rate for conventional 2D imaging, and the imaging frame rate corresponding to the first imaging mode is a high frame rate for 2D imaging.

When the imaging mode of the movie file is the first imaging mode, the playback frame rate of the movie file is determined as the first playback frame rate according to the first imaging mode, so that the first playback frame rate is less than the imaging frame rate corresponding to the first imaging mode, and the movie file is played with the first playback frame rate, realizing the slow playback of the movie file. In this way, the movie file is played with a frame rate lower than the imaging frame rate, avoiding ineffective display of the detailed information in the images caused by too short dwell time on each frame of contrast-enhanced images due to too high playback frame rate, thus improving viewing experience.

In one embodiment, the first playback frame rate is less than the imaging frame rate corresponding to the first imaging mode, and the first playback frame rate is greater than or equal to the imaging frame rate corresponding to the second imaging mode. In this way, the range of the first playback frame rate is further limited, so as to avoid that the first playback frame rate is too small, resulting in poor viewing effect.

The playback of the movie file can be paused and further adjusted the playback frame rate by users according to their personal needs during playback.

In one embodiment, when the imaging mode of the movie file is determined as the second imaging mode, a second playback frame rate of the movie file determined according to the second imaging mode may be the second playback frame rate, and the second playback frame rate may be used to play the movie file; wherein the second playback frame rate is equal to the imaging frame rate corresponding to the second imaging mode.

The imaging mode of the movie file is the second imaging mode, which means that when viewing with the imaging frame rate corresponding to the imaging mode of the movie file, the frame rate is within the range of the frame rate that is more comfortable for the human eye. The imaging frame of the second imaging mode may be used by default. The playback frame rate of the movie file may also be modified by users according to their personal needs in actual usage.

In one embodiment, the imaging mode may further comprise a third imaging mode, an imaging frame rate corresponding to the third imaging mode is smaller than the imaging frame rate corresponding to the second imaging mode; and when the imaging mode of the movie file is determined as the third imaging mode, a third playback frame rate of the movie file according to the third imaging mode may be determined, and the third playback frame rate may be used to play the movie file.

In this embodiment, the third imaging mode may be 3D or 4D contrast-enhanced imaging. When the imaging mode of the movie file is the third imaging mode, it means that the imaging frame rate corresponding to the imaging mode of the movie file in this imaging mode is too low. When the movie file is played directly at the imaging frame rate in this imaging mode, a phenomenon of "not smooth" may be appeared, affecting the users' viewing experience. In order to improve the users' viewing experience, when playing the movie file obtained in the third imaging mode, the frame rate higher than the imaging frame rate (the third playback frame rate) is used for playing.

In one embodiment, the third playback frame rate is greater than the imaging frame rate corresponding to the third imaging mode and less than the imaging frame rate corresponding to the second imaging mode. In this way, the third playback frame rate is further limited to avoid ineffective display of the detailed information in the images caused by too short dwell time on each frame of contrast-enhanced images due to too high playback frame rate, thus improving viewing experience.

In one embodiment, determining a playback frame rate of the movie file according to the imaging mode may comprise: determining the playback frame rate according to the imaging frame rate corresponding to the imaging mode, and the playback frame rate being negatively correlated with the imaging frame rate of the ultrasound images.

In one embodiment, determining a playback frame rate of the movie file according to the imaging mode of the movie file may comprise: determining the playback speed level of the movie file according to the imaging frame rate corresponding to the imaging mode of the movie file; and determining the playback frame rate according to the playback speed level and the imaging frame rate of the ultrasound images, or taking the preset playback frame rate corresponding to the playback speed level as the playback frame rate.

The playback speed level is the same as the playback speed level in any of the above-mentioned embodiments. When the playback speed level is determined according to the imaging frame rate corresponding to the imaging mode of the movie file, a unique playback speed level or a plurality of candidate playback speed level or a candidate playback speed level interval can be determined according to a preset correspondence. The playback speed level can directly correspond to the playback speed or the playback frame rate.

The playback speed level may correspond to the preset playback frame rate, the preset playback frame rate corresponding to the first playback speed level is less than the imaging frame rate corresponding to the first imaging mode, the preset playback frame rate corresponding to the second playback speed level is equal to the imaging frame rate corresponding to the second imaging mode, and the preset playback frame rate corresponding to the third playback speed level is greater than the imaging frame rate corresponding to the third imaging mode.

In one embodiment, determining the playback speed level of the movie file according to the imaging frame rate corresponding to the imaging mode of the movie file may comprise: determining the playback speed level from a plurality of preset playback speed levels according to the imaging frame rate.

In one embodiment, determining the playback speed level from a plurality of preset playback speed level according to the imaging frame rate may comprise: determining candidate playback speed levels from the plurality of preset playback speed level according to the imaging frame rate; and determining the playback speed level from the candidate playback speed levels according to input information of a user input interface.

In one embodiment, before determining the playback speed level from the candidate playback speed level according to input information of a user input interface, the method may further comprise: displaying the candidate playback speed level.

In one embodiment, before determining the playback speed level from the candidate playback speed level according to input information of a user input interface, the method may further comprise: displaying the preset playback speed levels other than the candidate playback speed level under a first display mode; and displaying the candidate playback speed level under a second display mode; wherein the second display mode is different from the first display mode.

In one embodiment, the playback frame rate may include a first playback frame rate, a second playback frame rate and a third playback frame rate; and playing the movie file with the playback frame rate may comprise: playing the movie file in a loop manner with the playback frame rate.

In one embodiment, the playback frame rate may include a first playback frame rate, a second playback frame rate and a third playback frame rate; and when playing the current frame of the movie file with the playback frame rate may comprise: switching the playback mode of the movie file from an automatic playing mode to a manual playing mode based on a first switching instruction; and playing image frames of the movie file under the manual playing mode.

In one embodiment, playing image frames of the movie file under the manual playing mode may comprise: when a preset operation for a control panel is detected, in response to the preset operation, playing the image frames of the movie file at a playback speed corresponding to the preset operation, wherein the playback speed is positively correlated with an operating speed of the preset operation.

In one embodiment, a playing speed corresponding to the manual playing mode is lower than a playing speed corresponding to the automatic playing mode.

In one embodiment, the first imaging mode and the second imaging mode correspond to imaging in different time periods in same contrast-enhanced imaging performed on tissues.

In one embodiment, the first imaging mode is used in a wash-in stage of a contrast agent, and the second imaging mode is used in a stage other than the wash-in stage of the contrast agent.

In one embodiment, the wash-in stage of the contrast agent comprises a stage corresponding to formation of the contrast agent microbubbles.

Figure 4:
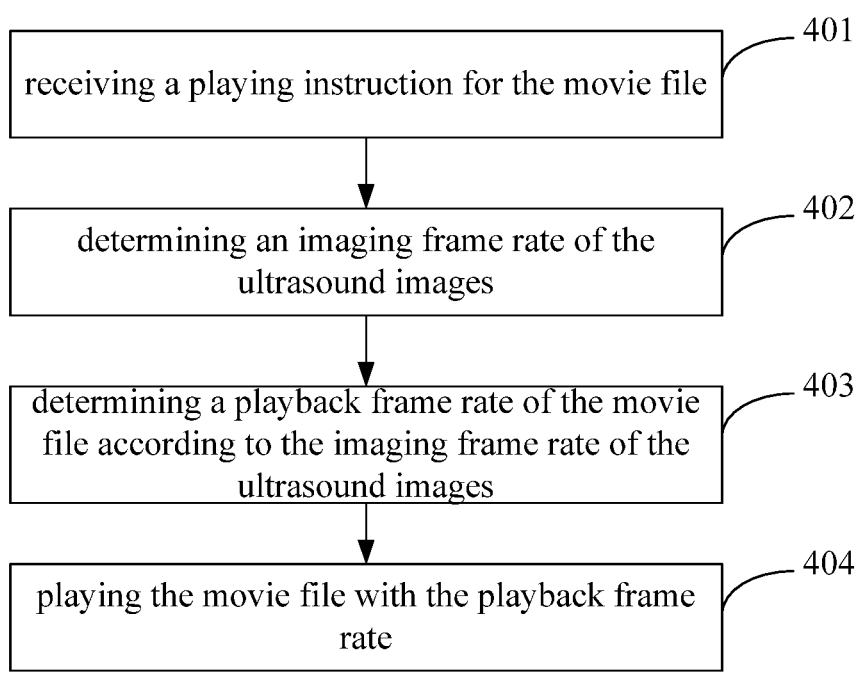
FIG. 4 is a schematic flowchart of a method of playing an ultrasound movie file in an embodiment.

Referring to FIG. 4, a method for playing an ultrasound movie file provided in one embodiment may include specific steps as follows:

Step 401: receiving a playing instruction for the movie file.

In this specific embodiment, the movie file is the dynamic data of ultrasound images, the ultrasound images is generated by ultrasound echoes which are acoustic signals returned from a target tissue to which ultrasound waves are transmitted by a probe of an ultrasound apparatus Step 402: determining an imaging frame rate of the ultrasound images.

Step 403: determining a playback frame rate of the movie file according to the imaging frame rate of the ultrasound images.

Step 404: playing the movie file with the playback frame rate.

Steps 401, 402 and 404 are basically the same as steps 201, 202 and 204, respectively, and will not be repeated here.

When determining the playback frame rate of the movie file according to the imaging frame rate of the ultrasound images, a negative correlation function between the imaging frame rate and the playback frame rate can be defined, wherein the imaging frame rate is the input of the negative correlation function, and the playback frame rate is the output of the negative correlation function. A function among the imaging frame rate, playback speed, and playback frame rate may also be defined, wherein the imaging frame rate and playback speed are the inputs of the function, and the playback frame rate is the output of the function. The imaging frame rate may be determined according to the imaging mode of the ultrasound apparatus 10, and the playback speed may be user-defined or selected from preset playback speeds. The playback speed may be customized or selected by users to meet their personal usage habits according to their personal needs, improving the usage experience.

In one embodiment, step 402 may include: determining a playback speed level; and determining a playback frame rate according to the playback speed level and the imaging frame rate of the ultrasound images. The playback speed level may be user-defined or selected by users from speed levels stored on the ultrasound apparatus 10. Alternatively, the playback speed level corresponding to the imaging frame rate may be directly obtained on the ultrasound apparatus 10 on the direct grounds of the corresponding relationship between the imaging frame rate and the playback speed level. The way to calculate the playback frame rate according to the playback speed level and the imaging frame rate of the ultrasound images is the same as that in the above-mentioned calculation method.

In one embodiment, determining the playback speed level may include: determining the playback speed level through a user input interface; or acquiring a preset speed playback level.

In one embodiment, determining the playback frame rate of the movie file according to the imaging frame rate of the ultrasound images may include: filtering candidate parameters from preset parameters according to the imaging frame rate, wherein the preset parameters are the preset playback speed levels or the preset playback frame rate; and determining the playback frame rate according to the candidate parameters. The range of preset parameters is limited by the size of the imaging frame rate, which is convenient for users to choose.

In one embodiment, before determining the playback frame rate according to the candidate parameters, the method may further comprise: displaying the candidate parameters.

In one embodiment, before determining the playback frame rate according to the candidate parameters, the method may further comprise: displaying the preset parameters other than the playback frame rate under a first display mode; and displaying the candidate parameters under a second display mode; wherein the second display mode is different from the first display mode.

In one embodiment, the imaging frame rate is negatively correlated with the candidate parameters. The range of the preset parameters is limited by the size of the imaging frame rate, which is convenient for users to select. The playback effect is better when the imaging frame rate is negatively correlated with the candidate parameters.

In one embodiment, when the preset parameters are the preset playback speed levels, filtering out the candidate parameters from the preset parameters according to the imaging frame rate may include: filtering out candidate playback speed level from the preset playback speed levels according to the imaging frame rate; and determining the playback frame rate according to the candidate parameters may include: determining a target playback speed level from the candidate playback speed level, and calculating the playback frame rate according to the target playback speed level and the imaging frame rate.

Figure 5:
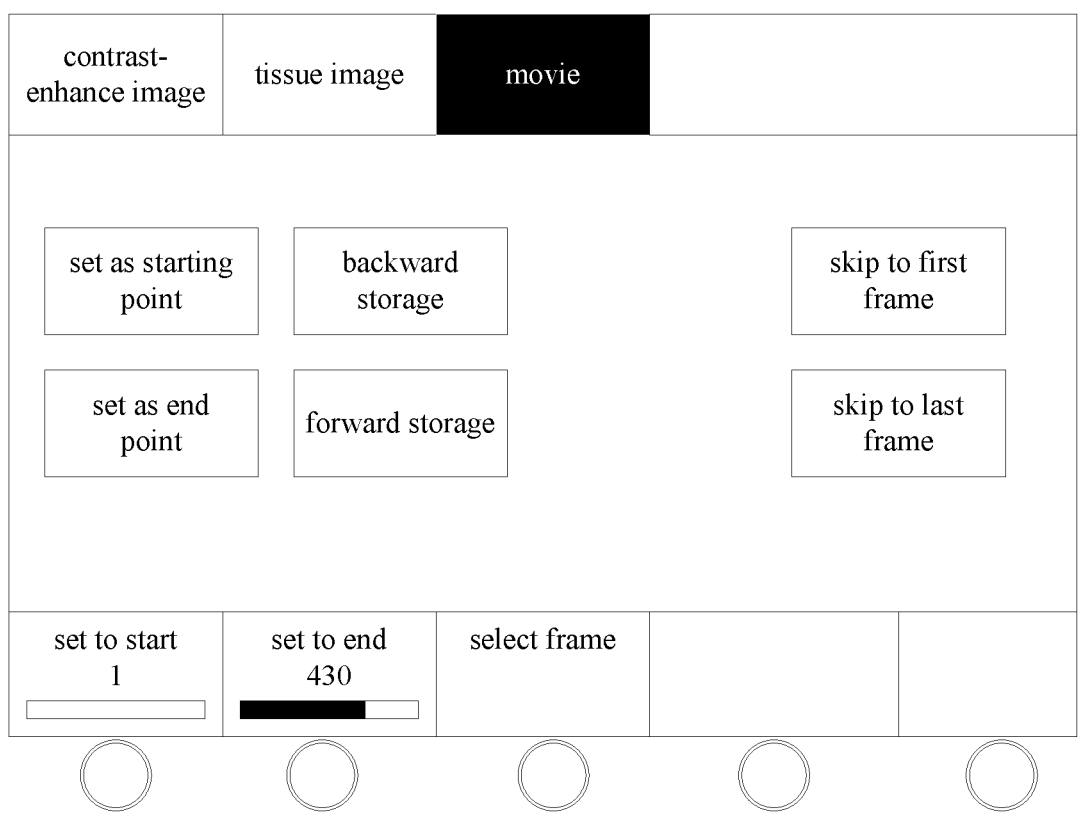
FIG. 5 is an example of a touch screen operating interface in manual mode in an embodiment.

In a specific embodiment, the method for playing an ultrasound movie file has two playback modes, a manual playing mode and an automatic playing mode; and specific steps of the two playback modes may be as follows:

1. Manual Mode:

By browsing the ultrasound images (shown as contrast-enhanced images in FIG. 5) frame by frame with slowly rolling the trackball of the ultrasound apparatus 10 or slowly turning the knob on the panel, an adjacent image of a current displayed image may be updated to display on the display 106. The scrolling step of the knob or the trackball may be customized, for example, the customized step may be set as one frame (volume) or two frames (volumes) of ultrasound images. When there is a need to browse the ultrasound images fast forward or backward by doctors, it can be achieved by quickly rolling the trackball or spinning the knob; in this respect, a corresponding image frame can be updated to display according to the user's operation speed, the faster the speed, the faster the update, which is similar to fast playback. Both the trackball and the knob of the apparatus can realize manual browsing of dynamic contrast-enhanced imaging data; and the browsing speed varies accordingly with the operation speed of the user. FIG. 4 is an example of a touch screen operation interface in manual mode. A "Select Frame" knob shown in the figure may be select ultrasound images frame by frame for reviewing and browsing.

Figure 6:
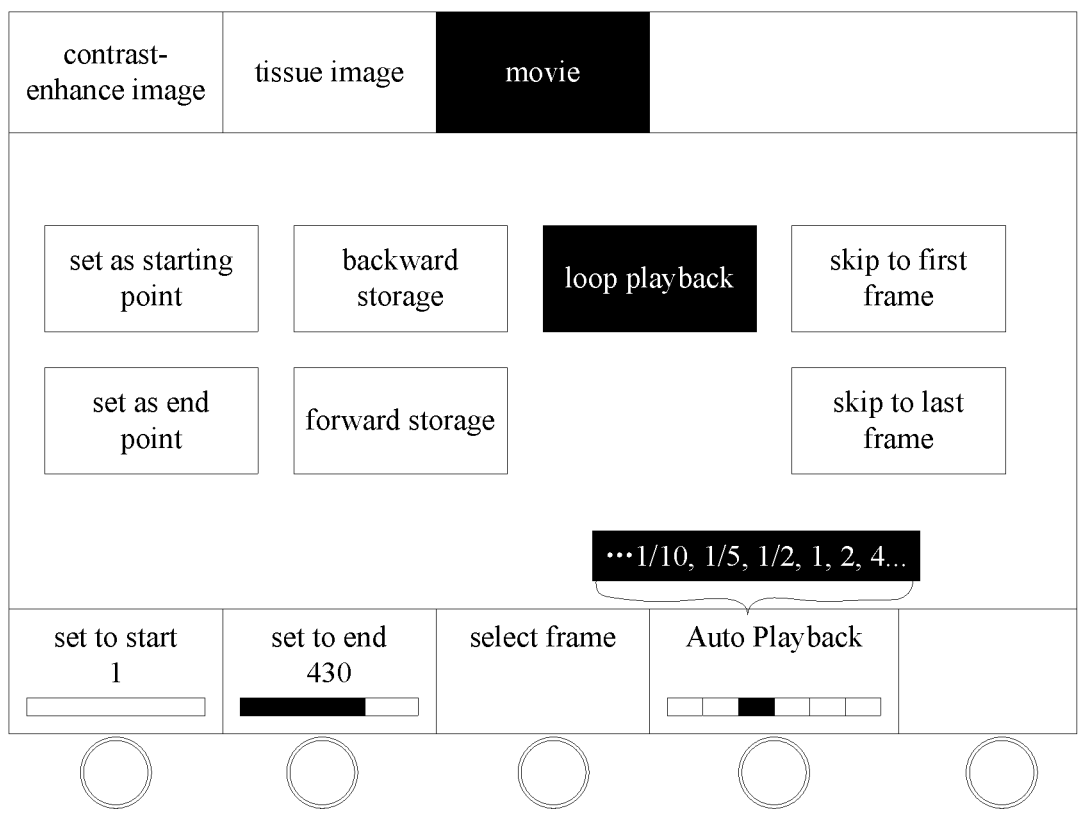
FIG. 6 is an example of a touch screen operating interface in manual mode in an embodiment.

2. Automatic Mode:

After opening the movie file to be browsed, the dynamic ultrasound image (shown as a contrast-enhanced image in FIG. 6) can be automatically played through a button of the touch screen of the ultrasound apparatus 10, and the playback speed can be selected. Playing with 1× speed may be equivalent to playing with the frame rate at which the dynamic contrast-enhanced imaging data was stored. When the playback speed is greater than 1×, the effect observed by the user is similar to "fast-motion playback". When the playback speed is less than 1×, the effect observed by the user is similar to "slow-motion playback". The setting of playback speed can be selected by knobs or buttons. FIG. 6 is an example of a touch screen operation interface in the automatic mode.

For an "Auto Playback" knob shown in the figure, when it is pressed, it means whether to play or not, and when it is rotated, it means to select a playback speed. For example, the playback speed of a movie in this example may be selected from six choices, including $\frac{1}{10}$, $\frac{1}{5}$, $\frac{1}{2}$, 1, 2, 4. In some embodiments, a "loop play" button 604 shown on the touch screen may represent that the system may automatically skip to the start frame to continue playing every time it plays to the end frame, thus it may play repeatedly.

The automatic mode may be implemented by specific steps as follows:

For dynamic data (movie file) stored under the condition of ordinary 2D contrast-enhanced imaging, when it is reviewed and browsed by users, the imaging frame rate adopted at the time of imaging is used as the playback frame rate by default for playback.

For dynamic data stored under the condition of high frame rate contrast imaging, when it is reviewed and browsed by users, the automatic playback may be played at a speed lower than 1× speed. The speed may be automatically calculated according to the imaging frame rate used at the time of storage, and the resulted playback frame rate is less than the imaging frame rate. For example, the automatic playback speed (speed gear)=1/(frame rate/15), and when the imaging frame rate is 75 FPS (75 frames per second), ⅕ times the playback speed may be used for play.

For dynamic data (such as 4D contrast-enhanced tubal ultrasound images) stored at a very low frame rate, when it is reviewed and browsed by users, the automatic playback may be played at a speed higher than 1× speed. The speed may be automatically calculated according to the imaging frame rate/volume rate used at the time of storage, and the resulted playback frame rate is greater than the imaging frame rate. For example, the automatic playback speed=1/(volume rate/3), and when the 4D imaging volume rate is 1.5 VPS, 2 times the playback speed may be used.

In a specific embodiment, a closest speed level can be selected for playback according to the calculation result of automatic playback speed, and it may also be played directly according to the calculated speed.

Descriptions are made herein with reference to various exemplary embodiments. However, those skilled in the art will recognize that changes and modifications may be made to the exemplary embodiments without departing from the scope of this disclosure. For example, the various operational steps, and the components used to perform the operational steps, may be implemented in different ways depending on the specific application or considering any number of cost functions associated with the operation of the system (for example, one or more steps may be deleted, modified or combined into other steps).

Additionally, as understood by those skilled in the art, the principles herein may be reflected in a computer program product on a computer-readable storage medium preloaded with computer-readable program code. Any tangible, non-transitory computer-readable storage medium may be used, including magnetic storage devices (hard disks, floppy disks, etc.), optical storage devices (CD-ROMs, DVDs, Blu Ray disks, etc.), flash memory, and/or the like. These computer program instructions may be loaded on a general purpose computer, a special purpose computer or other programmable data processing apparatus to form a machine such that the instructions executed on the computer or other programmable data processing apparatus may generate means for implementing the specified functions. These computer program instructions may also be stored in a computer-readable memory that instructs a computer or other programmable data processing device to operate in a specific manner, such that the instructions stored in the computer-readable memory may form a manufactured product, including means for implementing specified functions. Computer program instructions may also be loaded on a computer or other programmable data processing device to perform a series of operational steps on the computer or other programmable device to produce a computer-implemented process such that the instructions executed on the computer or other programmable equipment can provide steps for realizing specified functions.

Although the principles herein have been shown in various embodiments, many modifications may be made in structures, arrangements, proportions, elements, materials and components that are particularly applicable to specific environmental and operational requirements to use without departing from the principles and scope of the present disclosure. The above modifications and other changes or amendments are intended to be included within the scope of this specification.

The foregoing detailed description has been described with reference to various embodiments. However, those skilled in the art will recognize that various modifications and changes can be made without departing from the scope of the present disclosure. Accordingly, this disclosure is to be considered in an illustrative rather than a restrictive sense, and all such modifications are intended to be included within its scope. Likewise, the advantages, other advantages, and solutions to problems of the various embodiments have been described above. However, the benefits, advantages, solutions to the problems, and any elements that give rise to these elements, or make them more explicit, should not be construed as critical, necessary, or essential. The term "comprising" and any other variants thereof used herein are non-exclusive inclusions, such that a process, method, article or device that includes a list of elements includes not only these elements, but also other elements that are not explicitly listed or do not belong to the process, method, system, article or device. In addition, the term "coupling" and any other variation thereof as used herein refer to physical connections, electrical connections, magnetic connections, optical connections, communication connections, functional connections, and/or any other connections.

Those skilled in the art may recognize that many changes may be made to the details of the above-described embodiments without departing from the underlying principles of the present invention. Accordingly, the scope of the present invention should be determined in accordance with the following claims.

The invention claimed is:

1. A method for playing a contrast enhanced ultrasound movie file, comprising:
    receiving a playing instruction for the movie file; the movie file being a dynamic data of contrast-enhanced images, the contrast-enhanced images being generated by ultrasound echoes which are acoustic signals returned from a target tissue to which ultrasound waves are transmitted by a probe of a contrast-enhanced ultrasound apparatus according to an imaging mode, the imaging mode including a first imaging mode and a second imaging mode, and an imaging frame rate corresponding to the first imaging mode being greater than an imaging frame rate corresponding to the second imaging mode;
    determining an imaging mode of the movie file;
    determining a playback frame rate of the movie file according to the imaging mode of the movie file; and
    playing the movie file with the playback frame rate; when the imaging mode of the movie file is the first imaging mode, determining the playback frame rate of the movie file as a first playback frame rate according to the first imaging mode, wherein the first playback frame rate is less than the imaging frame rate corresponding to the first imaging mode, and the first playback frame rate is greater than or equal to the imaging frame rate corresponding to the second imaging mode.

2. The method according to claim 1, wherein when the imaging mode of the movie file is the second imaging mode,
    determining a playback frame rate of the movie file according to the imaging mode of the movie file and playing the movie file with the playback frame rate, comprise:
        determining a second playback frame rate of the movie file according to the second imaging mode, and using the second playback frame rate to play the movie file;

wherein the second playback frame rate is equal to the imaging frame rate corresponding to the second imaging mode.

3. The method according to claim 2, wherein the imaging mode further comprises a third imaging mode, an imaging frame rate corresponding to the third imaging mode is smaller than the imaging frame rate corresponding to the second imaging mode; and when the imaging mode of the movie file is the third imaging mode, determining a playback frame rate of the movie file according to the imaging mode of the movie file and playing the movie file with the playback frame rate, comprise:

determining a third playback frame rate of the movie file according to the third imaging mode, and using the third playback frame rate to play the movie file;

wherein the third playback frame rate is greater than the imaging frame rate corresponding to the third imaging mode and less than the imaging frame rate corresponding to the second imaging mode.

4. The method according to claim 1, wherein determining a playback frame rate of the movie file according to the imaging mode of the movie file comprises:

determining a playback speed level of the movie file according to the imaging frame rate corresponding to the imaging mode of the movie file; and determining the playback frame rate according to the playback speed level and the imaging frame rate, or taking a preset playback frame rate corresponding to the playback speed level as the playback frame rate.

5. The method according to claim 4, wherein determining a playback speed level of the movie file according to the imaging frame rate corresponding to the imaging mode of the movie file comprises:

determining the playback speed level from a plurality of preset playback speed levels according to the imaging frame rate.

6. The method according to claim 5, wherein determining the playback speed level from a plurality of preset playback speed levels according to the imaging frame rate comprises:

determining a candidate playback speed level from the plurality of preset playback speed levels according to the imaging frame rate; and determining the playback speed level from the candidate playback speed level according to input information of a user input interface.

7. The method according to claim 6, wherein before determining the playback speed level from the candidate playback speed level according to input information of a user input interface, the method further comprises:

displaying the preset playback speed levels other than the candidate playback speed level under a first display mode; and displaying the candidate playback speed level under a second display mode;

wherein the second display mode is different from the first display mode.

8. The method according to claim 1, wherein playing the movie file with the playback frame rate comprises:

playing the movie file in a loop manner with the playback frame rate.

9. The method according to claim 1, wherein during playing the movie file with the playback frame rate, the method further comprises:

switching a playback mode of the movie file from an automatic playing mode to a manual playing mode based on a first switching instruction; and playing image frames of the movie file under the manual playing mode;

wherein playing image frames of the movie file under the manual playing mode comprises:

when a preset operation for a control panel is detected, in response to the preset operation, playing the image frames of the movie file at a playback speed corresponding to the preset operation, wherein the playback speed is positively correlated with an operating speed of the preset operation.

10. The method according to claim 9, wherein a playing speed corresponding to the manual playing mode is lower than a playing speed corresponding to the automatic playing mode.

11. The method according to claim 1, wherein the first imaging mode and the second imaging mode correspond to imaging in different time periods in same contrast-enhanced imaging performed on tissues.

12. The method of claim 11, wherein the first imaging mode is used in a wash-in stage of a contrast agent, and the second imaging mode is used in a stage other than the wash-in stage of the contrast agent.

13. The method of claim 12, wherein the wash-in stage of the contrast agent comprises a stage corresponding to formation of contrast agent microbubbles.

14. An ultrasound device, comprising a probe, a transmitting circuit, a receiving circuit, a beam synthesis circuit, a memory, and a processor configured to:

receive a playing instruction for a movie file; the movie file being a dynamic data of contrast-enhanced images, the contrast-enhanced images being generated by ultrasound echoes which are acoustic signals returned from a target tissue to which ultrasound waves are transmitted by a probe of a contrast-enhanced ultrasound apparatus according to an imaging mode, the imaging mode including a first imaging mode and a second imaging mode, and an imaging frame rate corresponding to the first imaging mode being greater than an imaging frame rate corresponding to the second imaging mode;

determine an imaging mode of the movie file;

determine a playback frame rate of the movie file according to the imaging mode of the movie file; and a display configured to play the movie file with the playback frame rate; when the imaging mode of the movie file is the first imaging mode, determining the playback frame rate of the movie file as a first playback frame rate according to the first imaging mode, wherein the first playback frame rate is less than the imaging frame rate corresponding to the first imaging mode, and the first playback frame rate is greater than or equal to the imaging frame rate corresponding to the second imaging mode.

* * * * *